United States Patent
van Lune et al.

(10) Patent No.: US 6,503,723 B1
(45) Date of Patent: Jan. 7, 2003

(54) METHOD FOR DETECTING ATP

(75) Inventors: Harry van Lune, Groningen (NL); Jan ter Wiel, Loppersum (NL)

(73) Assignee: Packard Bioscience B.V., Groningen (NL)

( * ) Notice: Subject to any disclaimer, the term of this patent is extended or adjusted under 35 U.S.C. 154(b) by 0 days.

(21) Appl. No.: 09/806,165

(22) PCT Filed: Sep. 30, 1999

(86) PCT No.: PCT/NL99/00606

§ 371 (c)(1),
(2), (4) Date: Jun. 22, 2001

(87) PCT Pub. No.: WO00/18953

PCT Pub. Date: Apr. 6, 2000

(30) Foreign Application Priority Data

Sep. 30, 1998 (NL) .............................. 1010224

(51) Int. Cl.[7] .............................. C12Q 1/66; C12Q 1/00; G01N 33/53
(52) U.S. Cl. .............................. 435/8; 435/6; 435/968; 435/975
(58) Field of Search .............................. 435/8, 4, 968, 435/975

(56) References Cited

U.S. PATENT DOCUMENTS 4,246,340 A  *  1/1981  Lundin et al. ................. 435/8
5,618,682 A      4/1997  Scheirer
5,650,289 A  *  7/1997  Wood ............................. 435/8
5,744,320 A      4/1998  Sherf et al.

OTHER PUBLICATIONS

Denburg, J.L. et al. "Anion Inhibition of Firefly Luciferase" *Archives of Biochemistry and Biophysics.* Dec. 1, 1970, pp. 668–675, vol. 141, No. 2.

Deluca, M. et al. "Purification and Properties of Firefly Luciferase" *Methods in Enzymology,* Jan. 1, 1978, pp. 3–15, vol. 57.

* cited by examiner

*Primary Examiner*—Louise N. Leary
(74) *Attorney, Agent, or Firm*—Leydig, Voit & Mayer, Ltd.

(57) ABSTRACT

The invention provides a method for detecting ATP in a sample, wherein the sample is contacted with a reaction mixture to effect a light signal, the reaction mixture comprising luciferin, luciferase and one or more water-soluble salts, the total salt concentration being at least 0.05 mole/liter, and wherein the light signal is measured. A kit is described for detecting ATP in a sample comprising luciferin, luciferase and a buffer solution comprising salts. A composition for detecting ATP in a sample comprising a total salt concentration of at least 0.05 mole/liter for prolonging a light signal occurring in a luciferin-luciferase reaction is also provided.

18 Claims, 7 Drawing Sheets

METHOD FOR DETECTING ATP

FIELD OF THE INVENTION

The invention relates to a method for detecting ATP and to a kit for use in this method.

BACKGROUND OF THE INVENTION

A known method for detecting ATP (adenosine triphosphate) utilizes bioluminescence. The bioluminescence of luciferase/luciferin organisms is known, wherein luciferin is converted into oxyluciferin. This conversion is catalyzed by the enzyme luciferase.

A known luciferase originates from the firefly, *Photinus pyralis*. This luciferase is an enzyme having a molecular weight of about 60,000 dalton and containing about 550 amino acids. The substrate for this enzyme is luciferin, also originating from the firefly. This is a polyheterocyclic organic acid, D-(−)-2-(6′-hydroxy-2′-benzothiazolyl)-$\Delta^2$-thiazoline-4-carboxylic acid.

It is assumed that the luciferase-catalyzed bioluminescence-reaction proceeds as follows:

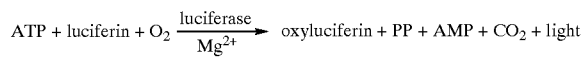

Here, PP stands for pyrophosphate and AMP stands for adenosine monophosphate. The oxyluciferin is initially produced in an excited state. When the substance returns into its ground state, this is accompanied by the emission of light.

When ATP is present in a medium, the amount of ATP can be determined by means of the luciferin-luciferase reaction. When ATP or an ATP-containing medium is added to a composition containing luciferin, luciferase, magnesium ions and oxygen, a brief intense light signal is obtained, depending on the selected composition of the reagents. For a few seconds, one may speak of a relatively stable light signal. It is assumed that the decrease in the rate of the reaction is caused by a product inhibition.

When, by means of an injection system, an ATP-containing sample is added to the composition containing the reagents for the luciferin-luciferase reaction, the concentration of ATP in the sample can be determined. The drawback of the measuring system is that when a microtiter plate is used, each well must be measured separately, i.e. well by well. This is a particularly time-consuming business. When an ATP-containing sample is added to a number of reaction vessels or wells of microtiter plates, followed by measuring, the light signal of the last vessels or wells that are measured will already have disappeared entirely or largely.

Therefore, it is preferred that a relatively stable light signal be obtained in the luciferin-luciferase reaction. When the light signal is stable for a longer time, use can be made of plate luminometers which do not require an injection system. Moreover, one may then prepare a large number of reaction vessels or microtiter plates, to measure the light signal only some time later. The light signal then remains normative for the amount of ATP in the various samples.

The object of the invention is to provide a method for determining the concentration of ATP by means of the luciferin-luciferase reaction, wherein the duration of the light emission during the reaction is prolonged significantly.

In the literature, many attempts to influence and prolong the duration of the light signal in the luciferase reaction have already been described.

One approach which influences the kinetics of the luciferin-luciferase reaction and prolongs the time of the light emission utilizes an inhibitor for the luciferase enzyme. An example of an inhibitor which has received much attention is arsenate. Arsenate decreases the intensity of the flash and also prolongs the length thereof. However, the sensitivity of the reaction for detecting ATP decreases as well. Also, the use of arsenate is less desirable from an environmental viewpoint. Moreover, the decrease of the intensity of the light signal is considered undesirable, in particular when microtiter plates or instruments capable of reading out strips are used.

The kinetics of the luciferin-luciferase reaction have been studied by DeLuca et al. in Analytical Chemistry, 95, 194–198, 1979. The effects of the addition of arsenate and other ions are demonstrated by the authors. However, a drawback of the method proposed is the non-linear relation of the decrease of the light intensity over a wide concentration range of ATP determination.

U.S. Pat. No. 5,618,682 describes a method for detecting luciferase, wherein a reaction mixture containing ATP is used. The reaction mixture contains, in addition to ATP, adenosine monophosphate, a radical catcher (DTT), dithiothreitol and a chelating agent (EDTA). A protease inhibitor, such as phenylacetic acid, is used as well.

Another approach opts for the use of co-enzyme A (CoA). In Biochimica et Biophysica Acta, vol. 27 (1958), 519–532, Airth et al. have described that the addition of CoA to a luciferin-luciferase reaction mixture has no effect on the light flash, but that the intensity of the light signal after the flash remains at a higher level for a longer time.

This approach is also opted for in U.S. Pat. No. 5,650,289, which proposes techniques and compositions of reaction mixtures which influence the kinetics of the luciferin-luciferase reaction. The techniques described are based on the use of CoA and DTT. The half-life of the light signal, i.e. the time after which 50% of the original light signal is observed, is assessed at 300 to 500 seconds.

U.S. Pat. No. 4,246,340 likewise proposes a method for obtaining a half-life of the light signal in a luciferin-luciferase reaction of a few minutes. The method described is based on the use of inhibitors, such as D-luciferin analoga. An example hereof is L-luciferin.

As mentioned, the object of the present invention is to provide an improved method for detecting ATP by means of the luciferin-luciferase reaction, while a light signal is obtained which lasts significantly longer than is described in the prior art. In addition, it is an object of the invention to provide that the intended method is simple and can be performed in a well of a microtiter plate.

BRIEF SUMMARY OF THE INVENTION

The invention is related to a method for detecting ATP in a sample, wherein the sample is contacted with a reaction mixture to effect a light signal, the reaction mixture comprising luciferin, luciferase and one or more water-soluble salts, the total salt concentration being at least 0.05 mole/liter, and wherein the light signal is measured.

DETAILED DESCRIPTION OF THE INVENTION

Figure 1:
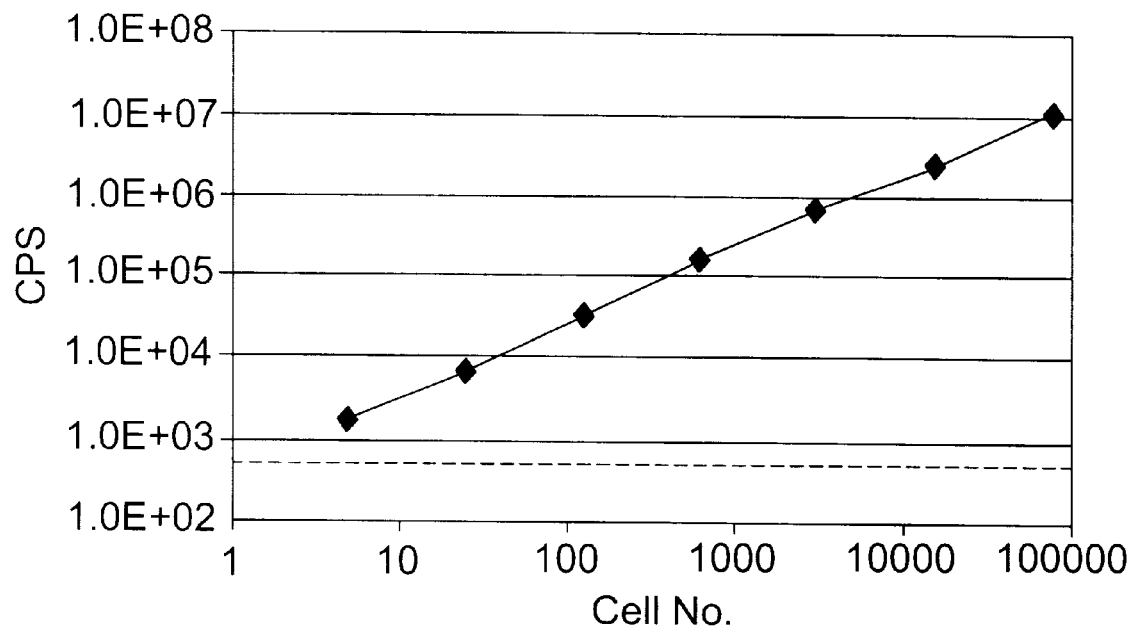
FIG. 1 is a graph demonstrating the relation between cell number (X-axis) and light intensity measured in counts per second (Y-axis).

Surprisingly, it has been found that the objects set are achieved by performing a luciferin-luciferase reaction in the presence of relatively large amounts of anions and cations originating from added salts. The anions and cations effect a non-competitive inhibition of the luciferase enzyme, whereby the duration of the light signal is prolonged to a half-life of at least 30 minutes, up to more than 8 hours.

Hence, the invention relates to a method for detecting ATP in a sample, wherein the sample is contacted with a reaction mixture to effect a light signal, the reaction mixture comprising luciferin, luciferase and one or more water-soluble salts, the total salt concentration being at least 0.05 mole/liter, and wherein the light signal is measured.

In the detection of ATP according to the invention, it has turned out that the light signal occurring in the luciferin-luciferase reaction, hence when ATP is present, has a half-life of from 30 minutes up to more than 8 hours. Although, according to the present method, ATP can accurately and simply be determined in any suitable type of container, it has been found that the method can be applied in a particularly suitable manner in the wells of microtiter plates or in liquid scintillation counters.

By luciferase is meant an enzyme catalyzing the oxidation of luciferin, which oxidation involves the production of a light signal. Luciferase can be isolated from organisms which produce luciferase. Luciferase can also be recovered from cells transformed or transfected with a polynucleotide coding for a luciferase. Preferably, a luciferase of the firefly *Photynus pyralis* is used.

By luciferin is meant the substance D-(−)-2-(6'-hydroxy-2'-benzothiazolyl)-$\Delta^2$-thiazoline-4-carboxylic acid. Luciferin can also be isolated from nature. However, it is preferred that synthetically prepared luciferin be used, because of the accessibility and the higher purity which this form typically has.

As mentioned, according to the invention, a sample for which the presence of ATP is to be assessed, is contacted with a reaction mixture comprising luciferin, luciferase and one or more water-soluble salts.

In said reaction mixture, luciferin will usually be present in an amount of between 0.01 and 1 mM, preferably between 0.05 and 0.5 mM. The enzyme luciferase will usually be present in an amount of between 0.0003 and 0.05, preferably between 0.001 and 0.03 gram per liter of the reaction mixture.

Preferably, the reaction mixture also contains magnesium ions. The magnesium ions will be present in an amount of at least 0.0005 mole per liter. Usually, the amount of magnesium ions will not be greater than 0.2 mole per liter.

The total amount of salts present in the reaction mixture is at least 0.05 mole/liter, and preferably at least 0.10 mole per liter. It has been found that the presence of a large amount of salts leads to a prolongation of the light signal occurring in the luciferin-luciferase reaction up to half an hour or more.

The amount of salts in the reaction mixture depends of course on the extent to which the ions of the salts are capable of causing inhibition of luciferase. Further, it is important that the salts dissolve entirely in the reaction mixture. The maximal amount of salts that is used will therefore particularly be determined by the solubility of the selected salts.

In principle, all water-soluble salts are eligible. Examples of suitable salts are alkali salts or alkaline earth salts of $Cl^-$, $Br^-$, $SO_4^{2-}$, $HSO_4^{2-}$, $HPO_4^-$, $H_2PO_4^-$, $NO_3^-$, and $HCO_3^{31}$. Good results are obtained with salt solutions of $Na_2HPO_4$, $NaH_2PO_4$ and $NaCl$. Preferably, the concentration of NaCl in the reaction mixture is about 100 mM.

Apart from the substances mentioned, the reaction mixture may contain all usual substances which are used in luciferin-luciferase reaction mixtures.

The reaction mixture preferably also comprises a suitable buffer, such as tricine, HEPPS, HEPES, MOPS, Tris, CHAPS or a phosphate salt. Preferably, HEPES or a mixture of said buffers is used. Such buffers can maintain the pH at a suitable value. Preferably, the pH is maintained at between 6.5 and 8.2. The amount of the buffer can be suitably selected by a skilled person and will usually range between 25 mM and 1M.

Further, the reaction mixture preferably comprises a stabilizer for the luciferase. Suitable examples of stabilizers are a serum albumin of a mammal, a lactalbumin and an ovalbumin. Preferably, Bovine Serum Albumin (BSA) is used. The amount of the stabilizer will be below 1 wt. %, calculated on the weight of the reaction mixture.

Further, the reaction mixture preferably comprises a sequestering agent such as EDTA or CDTA. Such substance is preferably present in an amount of 0.1 and 10 mM.

The sample which is contacted with the above-described reaction mixture can in principle be any sample in respect of which the presence of ATP is to be assessed. The ATP may, for instance, be present in dissolved form in a buffer solution.

In specific cases, the sample will be of a biological nature, for instance originating from a cell culture. Living cells contain ATP, as is known. If the sample contains cells, the sample should priorly be subjected to an cell lysis in order to release and be able to detect the ATP present in the cells. The amount of ATP is a measure for the amount of cells present.

A problem involved in the detection of ATP in a cell-containing sample is that cells usually contain ATP-consuming enzymes such as ATP-ases, which degrade the ATP to be detected and hence disturb the measuring. According to the invention, it has been found that the disturbing effect of any ATP-ases can be removed by performing the cell lysis in an alkaline medium, preferably utilizing a nonionic detergent. Particularly suitable lysing detergents proved to be nonylphenoxypolyethoxyethanol (Triton N101®) and Triton X-100.

Before the present invention was made, the decrease of the light signal during the determination of ATP by means of the luciferin-luciferase reaction varied from a number of percents per minute up to a decrease to half the original light signal within one minute. As a result of the fast decrease of light emission of the bioluminescence reaction for determining ATP, the use of determining ATP for, for instance, quantifying cell numbers has remained limited, because not only does the light signal decrease rapidly, but ATP-consuming enzymes also influence the light emission pattern and cause an even faster decrease of the light emission. By means of said cell lysis, the present invention provides a solution to this problem as well.

For performing the cell lysis, the sample is contacted with a lysing solution. This solution contains the lysing detergent in an amount of, preferably, 0.1–10 gram per liter. The pH of the solution is preferably above 9.5, particularly preferably above 10, and can suitably be set with a base such as sodium hydroxide. The incubation period required for performing the cell lysis can suitably be selected by a skilled person on the basis of his professional knowledge.

After the cell lysis, the sample is contacted with the above-described reaction mixture. This step is performed in the presence of oxygen, for instance on air. Preferably, both the cell lysis, if any, and the luciferin-luciferase reaction are performed in a well of a microtiter plate. To this end, preferably 100 $\mu$l of the possibly dissolved sample and 50 $\mu$l of the cell lysis mixture, followed by 50 $\mu$l of the reaction mixture, are put together.

As soon as the sample is contacted with the reaction mixture, a light signal will be emitted if ATP is present in the sample. This light signal gives a measure for the amount of ATP present in the sample. If the sample contains cells, the amount of ATP can be considered a measure for the amount of living cells that were present in the sample.

Measuring the light signal and, on the basis thereof, quantifying the amount of ATP, can be carried out in any known manner. For this, instruments such as the TopCount (Packard) or the Lumicount (Packard) can be used, or other plate luminometers adapted to measure microtiter plates. Also, so-called strip luminometers may be used, or luminometers provided with injection systems. Also, liquid scintillators may be used and other instruments capable of measuring the level of the resulting light signal.

To give the reaction kinetics of the luciferin-luciferase reaction time to stabilize, it is preferred that after the sample and the reaction mixture have been put together, one waits some time before the measuring is started. This time can suitably be determined by a skilled person and will usually range between 5 and 15 minutes.

The invention also relates to a kit for use in the above-described method for detecting ATP.

Due to their slight stability, luciferase and luciferin are preferably present in lyophilized form in the kit. To achieve this form, one may proceed as follows. A mixture of the desired amounts of luciferase and luciferin is dissolved in a buffer, for instance a PBS buffer. Preferably, a small amount of a stabilizer, such as BSA, is added thereto as well. The resulting composition can be lyophilized in the presence of a usual auxiliary agent, such as trehalose.

In addition to the above-described mixture of luciferin and luciferase, preferably in lyophilized form, the kit according to the invention comprises a buffer solution containing the other constituents of the above-described reaction mixture. In a preferred practical example, the kit also comprises the above-described lysing solution.

The invention will presently be specified on the basis of the following examples.

EXAMPLE 1

Test sensitivity and linearity of the ATPLite-M kit. Dilution series U937 (Human Promyelocyt), HeLa (Human Cervixcarcinoma), and CHO (Chinese Hamster Ovary) cells.

U937 cells were cultured in RPMI medium supplemented with Fetal Calf Serum (FCS) to 10% end concentration. HeLa cells were cultured in Dulbecco's Modified Eagles Medium (DMEM) supplemented with FCS to 10% end concentration. CHO cells were cultured in a 1:1 mixture of DMEM) and Ham's F12 medium supplemented with FCS to 5% end concentration in a 37° C. incubator in a 5% $CO_2$ atmosphere.

Adherent CHO and HeLa cells were washed with PBS without calcium salts and magnesium salts. The cells were released from the culture substrate by incubation with a thin layer of 1:10 diluted commercially available trypsin-EDTA solution and subsequently collected in culture medium+FCS. U937 suspension cells were centrifuged for 5 minutes at 500×g in a 50 ml Falcon tube. The cell pellet was included in fresh culture medium. The cell titer was determined by means of a Coulter Counter by counting a 1:20 dilution of the collected cell suspensions in an isotonic solution.

Serial dilutions of the cell suspensions were prepared in culture medium+FCS. Starting from cell suspensions having a titer of 781250 cells per milliliter, 1:5 dilutions were prepared to obtain dilution series of respectively 781250, 156250, 31250, 6250, 1250, 250 and 50 cells per milliliter. 100 microliter cell suspensions were pipetted into the wells of a 96-well microtiter plate. After two hours of incubation in an incubator, the cells were lysed by adding to each of the wells 50 microliter of Mammalian Cell Lysis Solution (solution D of Example 4) and shaking the lysates for two minutes on a shaking platform. After this, 50 microliter of ATP-M buffer (solution E of Example 4) was added to each well, to start the ATP-dependent luciferin-luciferase reaction. After one hour of incubation, the intensity of the released light in each well was determined by means of a Packard TopCount. The results are shown in FIGS. 1, 2 and 3.

Figure 2:
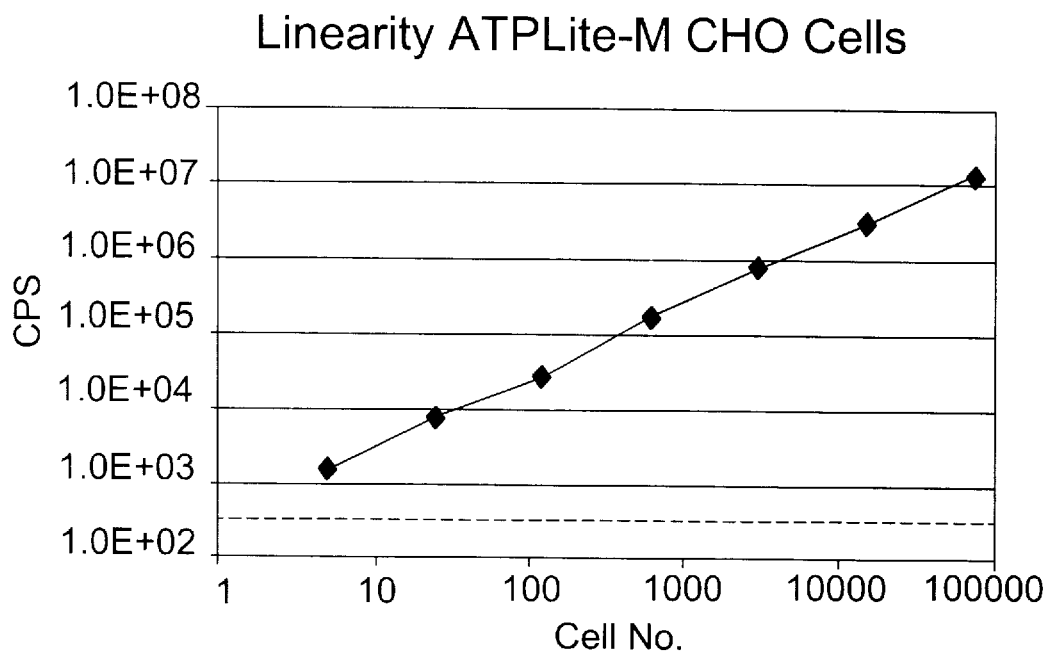
FIG. 2 is a graph demonstrating the relation between cell number (X-axis) and light intensity measured in counts per second (Y-axis).
Figure 3:
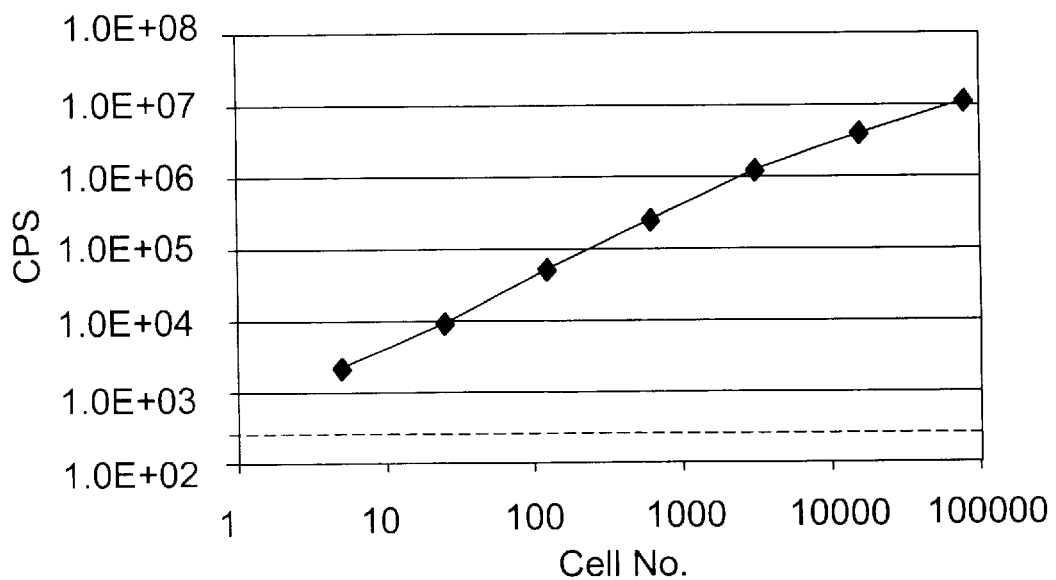
FIG. 3 is a graph demonstrating the relation between cell number (X-axis) and light intensity measured in counts per second (Y-axis).

FIGS. 1, 2 and 3 demonstrate that regardless of the cell line measured, there is a linear (cor)relation between the number of cells located in each well and the associated light intensity measured (expressed in counts per second). These results show that the number of cells present in a well to be sampled can accurately be determined by relating the light intensity measured to a standard line. Further, the light intensity measured proves to be directly proportional to the number of cells over a wide bandwidth of cell numbers.

Legend to the Figure

Linearity ATPLite-M assay during use of various cell lines. A dilution series of cells was prepared from a cell suspension. Cells (0; 5; 25; 125; 625; 3125; 15625; 78125) were added to wells of a 96-well plate. After two hours of incubation, 50 µl lysis solution was added. After lysis, 50 µl assay substrate buffer was added. Light intensity was measured by means of a Packard TopCount. The Figure shows on a double log scale the relation between the cell number (X-axis) and the light intensity measured (in counts per second (CPS, Y-axis). The dotted line in each graph indicates the background level of the assay.

The following examples/experiments demonstrate that with a simple formulation, a light signal can be obtained which slowly decreases in time. The signal is proportional to the concentration of ATP in the mixture to be measured.

EXAMPLE 2

For this purpose, a dilution series (1:10) was made of ATP in water from 1E-06 M through 1E-11M ATP. To 100 µl of each of these ATP solutions, 100 µl of solution A was added in wells of a white 96-well microplate and the light signal was repeatedly measured in time on a Packard TopCount for 4 hours.

| Formulation Solution A: | |
|---|---|
| HEPES | 50 mM |
| EDTA | 4 mM |
| MgCl$_2$ | 10 mM |
| NaCl | 260 mM |
| BSA | 1.50 gram per liter |
| Trehalose | 5.0 gram per liter |
| D-Luciferin | 0.2 mM |
| Luciferase | 6 mg per liter |
| pH set at 7.8 with NaOH | |

The final concentrations of the components of solution A and the ATP in the 1:1 mixture of solution A and the ATP solution become 2 times lower in the wells, due to the mixing of these two solutions.

The results are as follows:

| | Top Count CPS (counts per second) | | | | | | |
|---|---|---|---|---|---|---|---|
| Time | ATP concentration in Mole per liter | | | | | | |
| (minutes) | 5.00E-07 | 5.00E-08 | 5.00E-09 | 5.00E-10 | 5.00E-011 | 5.00E-12 | 0 |
| 0 | 18775000 | 1982067 | 195134 | 20115 | 2553 | 742 | 505 |
| 15 | 17535000 | 1839266 | 181276 | 18525 | 2071 | 379 | 204 |
| 30 | 16785000 | 1757748 | 173262 | 17671 | 1975 | 353 | 177 |
| 60 | 15660000 | 1648084 | 162572 | 16667 | 1819 | 305 | 139 |
| 90 | 14700000 | 1553360 | 152886 | 15739 | 1676 | 305 | 135 |
| 120 | 13795000 | 1461522 | 144238 | 14641 | 1549 | 274 | 122 |
| 150 | 12955000 | 1376604 | 135801 | 13854 | 1505 | 261 | 117 |
| 180 | 12135000 | 1292035 | 127490 | 12934 | 1434 | 242 | 117 |
| 210 | 11455000 | 1222251 | 120558 | 12274 | 1350 | 234 | 113 |
| 240 | 10830000 | 1155314 | 114113 | 11587 | 1265 | 217 | 103 |

Figure 4:
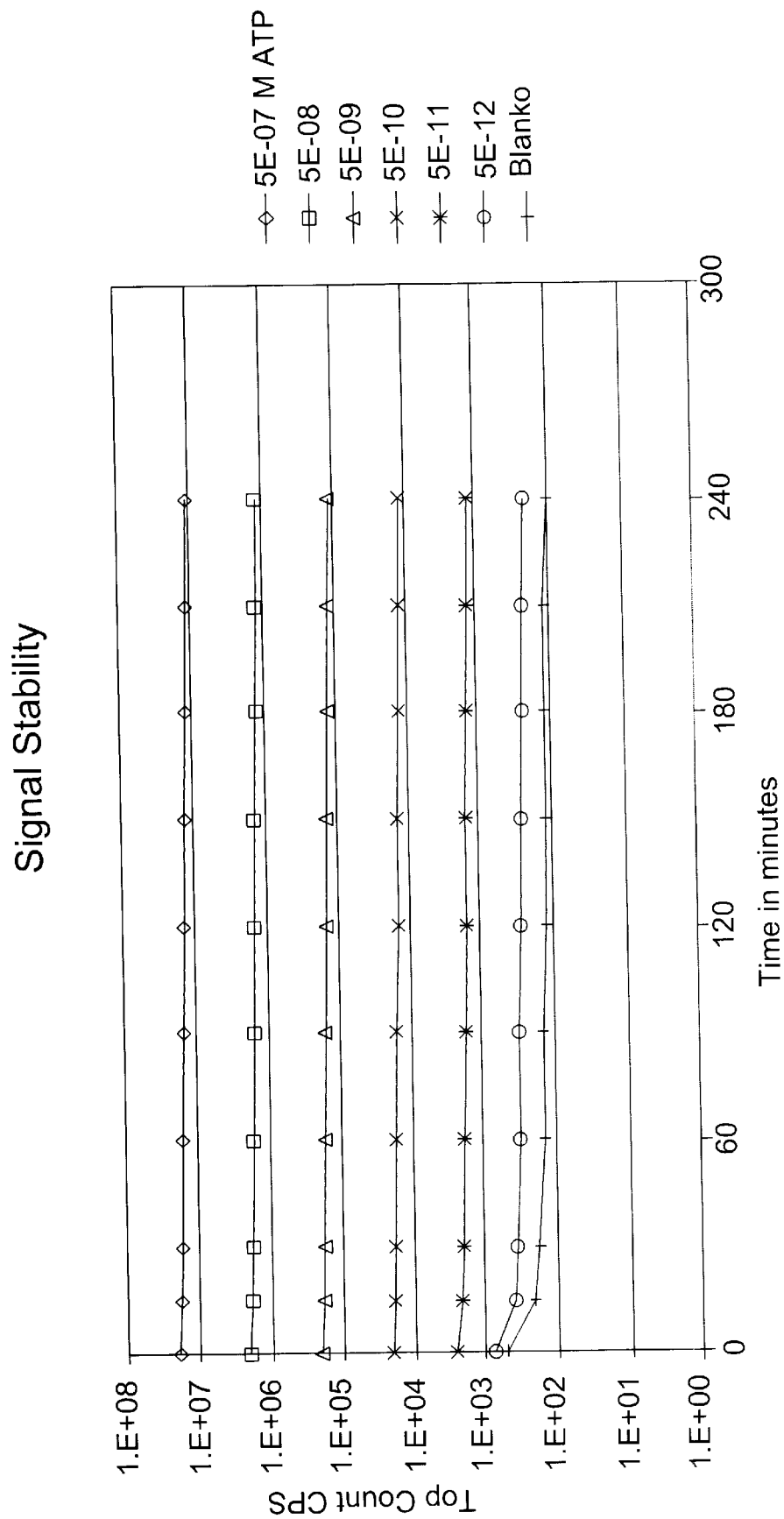
FIG. 4 is a graph demonstrating the relation between time measured in minutes (X-axis) and light intensity measured in counts per second (Y-axis).

From the results, it follows that the signal is to the concentration of ATP and that the signal reduces in time, it takes more than 4 hours before the signal has decreased to half the signal of the first measurement (see also FIG. 4).

EXAMPLE 3

For this purpose, a dilution series (1:10) was made of ATP in water from 1E-06 M through 1E-11 M ATP. To 100 µl of each of these ATP solutions, 100 µl of solution B was added in wells of a white 96-well microplate and the light signal was repeatedly measured in time on a Packard TopCount for 9.5 hours.

| Formulation Solution B: | |
|---|---|
| HEPES | 175 mM |
| EDTA | 2 mM |
| MgCl2 | 2 mM |
| NaCl | 100 mM |
| NaH2PO4 | 75 mM |
| BSA | 1.5 gram per liter |
| Trehalose | 5.0 gram per liter |
| D-Luciferin | 0.2 mM |
| Luciferase | 6 milligram per liter |
| Triton N-101 | 2.0 gram per liter |
| pH set at 7.4 with NaOH | |

The final concentrations of the components of solution B and the ATP in the 1:1 mixture of solution B and the ATP solutions become 2 times lower in the wells, due to the mixing of these two solutions.

The results are as follows:

| Time | Top Count CPS (counts per second) ATP concentration in Mole per liter | | | | | | |
|---|---|---|---|---|---|---|---|
| (minutes) | 5.00E-07 | 5.00E-08 | 5.00E-09 | 5.00E-10 | 5.00E-011 | 5.00E-12 | 0 |
| 0 | 13350000 | 1347570 | 136270 | 14221 | 2091 | 524 | 376 |
| 30 | 12393333 | 1256867 | 127691 | 13369 | 1597 | 404 | 292 |
| 60 | 11700000 | 1192631 | 121205 | 12775 | 1533 | 384 | 320 |
| 90 | 11063333 | 1134309 | 115303 | 12177 | 1461 | 360 | 258 |
| 120 | 10500000 | 1079513 | 110011 | 11573 | 1380 | 355 | 241 |
| 150 | 9934357 | 1024827 | 104686 | 11020 | 1314 | 337 | 232 |
| 180 | 9475816 | 980343 | 100124 | 10504 | 1246 | 323 | 215 |
| 210 | 9031766 | 935826 | 95537 | 10113 | 1198 | 307 | 216 |
| 240 | 8632510 | 897371 | 91619 | 9647 | 1130 | 298 | 196 |
| 270 | 8256822 | 859530 | 87607 | 9299 | 1101 | 277 | 190 |
| 300 | 7912674 | 825082 | 84268 | 8927 | 1042 | 261 | 175 |
| 330 | 7572644 | 791870 | 80809 | 8531 | 1010 | 262 | 169 |
| 360 | 7250944 | 758263 | 77532 | 8193 | 959 | 247 | 164 |
| 390 | 6949015 | 727838 | 74190 | 7828 | 943 | 242 | 157 |
| 420 | 6660917 | 698798 | 71069 | 7471 | 901 | 219 | 157 |
| 450 | 6382937 | 671368 | 68224 | 7192 | 844 | 208 | 144 |
| 480 | 6118376 | 643632 | 65336 | 6928 | 820 | 209 | 139 |
| 510 | 5874066 | 618683 | 62905 | 6608 | 785 | 197 | 137 |
| 540 | 5638346 | 594449 | 60334 | 6366 | 750 | 179 | 127 |
| 570 | 5416984 | 571113 | 57747 | 6134 | 716 | 186 | 124 |

Figure 5:
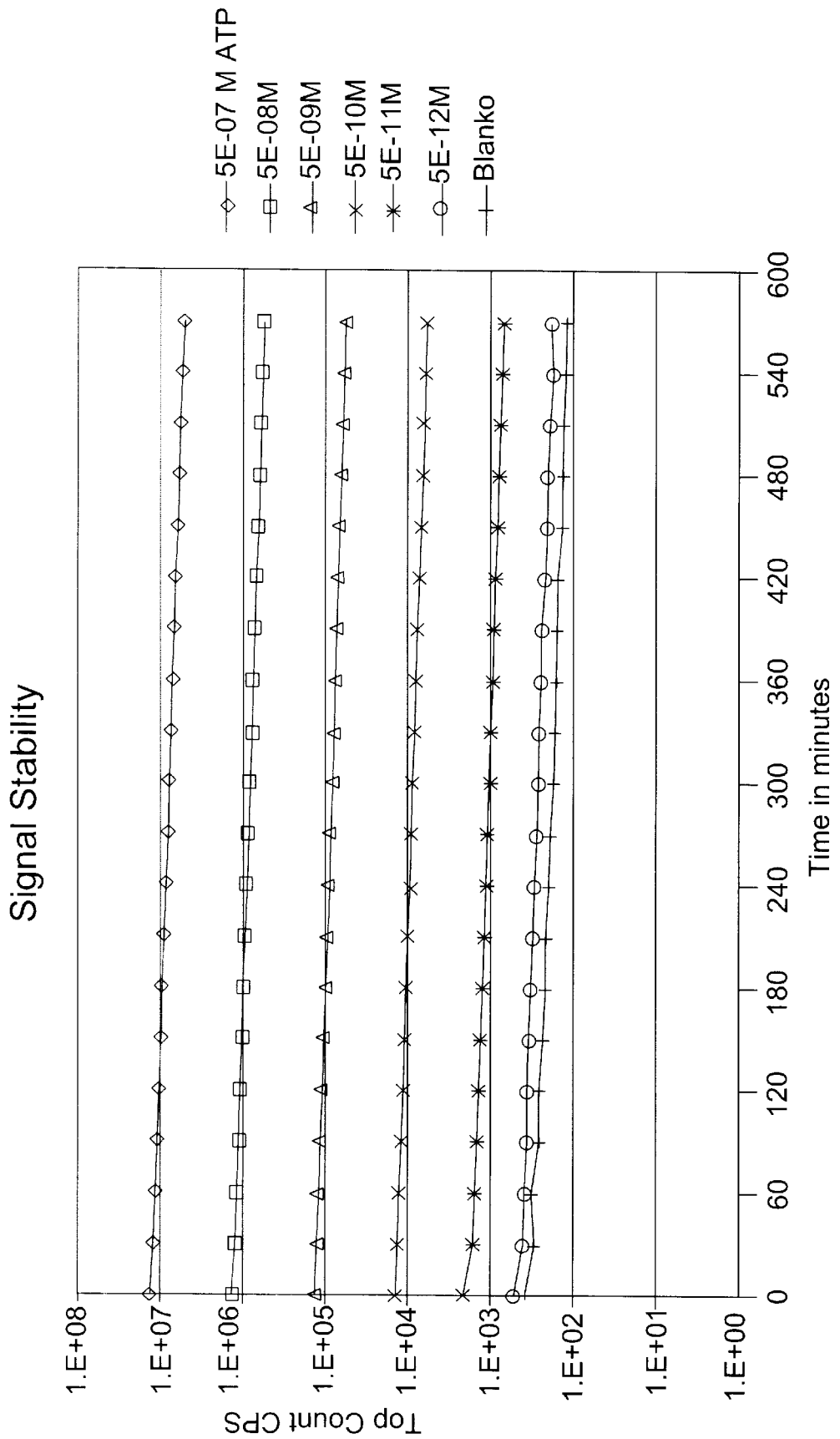
FIG. 5 is a graph demonstrating the relation between time measured in minutes (X-axis) and light intensity measured in counts per second (Y-axis).

From the results, it follows that the signal is linear to the concentration of ATP and that the signal slowly decreases in time, the half-life in this example being about 7 hours (see also FIG. 5).

EXAMPLE 4

For this purpose, a dilution series (1:2) was made from CHO (Chinese Hamster Ovary) cells in Dulbecco's MEM supplemented with Petal Calf Serum (FCS) to 10% end concentration from 37000 cells per 100 µl to 36 cells per 100 µl in a white "tissue culture treated" microplate. To 100 µl of each cell dilution, 100 µl of solution C was added and the ATP-dependent light signal was repeatedly measured in time on a Packard TopCount for 9.5 hours.

| Formulation Solution C: | |
|---|---|
| HEPES | 175 mM |
| EDTA | 2 mM |
| MgCl2 | 2 mM |
| NaCl | 65 mM |
| NaH2PO4 | 75 mM |
| BSA | 1.5 gram per liter |
| Trehalose | 5.0 gram per liter |
| D-Luciferin | 0.2 mM |
| Luciferase | 6 milligram per liter |
| Triton N-101 | 2.0 gram per liter |
| pH set at 7.4 with NaOH | |

The results are as follows:

| Time | Top Count CPS (counts per second) Cell number per 100 µl DMEM, 10% FKS | | | | | | | | | | | |
|---|---|---|---|---|---|---|---|---|---|---|---|---|
| (min) | 37000 | 18500 | 9250 | 4625 | 2313 | 1156 | 578 | 289 | 145 | 72 | 36 | 0 |
| 0 | 15960000 | 8418265 | 4754536 | 2432333 | 1231988 | 636875 | 333584 | 171599 | 90251 | 46440 | 25290 | 307 |
| 30 | 10543599 | 5818309 | 3514526 | 1829353 | 948150 | 494213 | 257975 | 133956 | 71035 | 36786 | 20003 | 232 |
| 60 | 7845328 | 4409567 | 2776537 | 1516077 | 798829 | 420828 | 220374 | 114631 | 61226 | 31897 | 17466 | 326 |
| 90 | 6081600 | 3499910 | 2300989 | 1304974 | 697804 | 371671 | 195253 | 101888 | 54620 | 28734 | 15716 | 384 |
| 120 | 4861105 | 2851444 | 1950778 | 1143700 | 619684 | 333162 | 176169 | 92174 | 49329 | 26481 | 14342 | 421 |
| 150 | 3969965 | 2354948 | 1672153 | 1011224 | 554333 | 301213 | 159991 | 83877 | 45045 | 24537 | 13194 | 478 |
| 180 | 3288088 | 1962123 | 1442805 | 899695 | 498440 | 273310 | 145935 | 76865 | 41211 | 23034 | 12292 | 557 |
| 210 | 2753856 | 1646775 | 1250622 | 805773 | 450312 | 249347 | 133912 | 70599 | 37878 | 21785 | 11425 | 601 |
| 240 | 2326726 | 1388681 | 1087504 | 720162 | 407623 | 227830 | 122869 | 64991 | 34916 | 20438 | 10603 | 652 |
| 270 | 1977520 | 1175021 | 946291 | 646642 | 368666 | 208627 | 112948 | 59850 | 32069 | 19261 | 9919 | 705 |
| 300 | 1689400 | 995294 | 825327 | 580632 | 335085 | 191058 | 103885 | 55207 | 29751 | 18112 | 9332 | 775 |
| 330 | 1451102 | 846160 | 719904 | 522876 | 304543 | 175235 | 95993 | 51077 | 27398 | 17061 | 8653 | 814 |
| 360 | 1250777 | 721240 | 628896 | 470660 | 277002 | 161169 | 88484 | 47213 | 25469 | 16006 | 8137 | 895 |

-continued

| Time | Cell number per 100 μl DMEM, 10% FKS | | | | | | | | | | |
|---|---|---|---|---|---|---|---|---|---|---|---|
| (min) | 37000 | 18500 | 9250 | 4625 | 2313 | 1156 | 578 | 289 | 145 | 72 | 36 | 0 |
| 390 | 1082119 | 617318 | 550186 | 423884 | 252183 | 148175 | 81697 | 43773 | 23414 | 15137 | 7675 | 960 |
| 420 | 939287 | 529036 | 481362 | 382755 | 229965 | 136601 | 75596 | 40654 | 21879 | 14198 | 7186 | 996 |
| 450 | 817431 | 455126 | 421545 | 345867 | 209675 | 125485 | 70111 | 37690 | 20180 | 13248 | 6803 | 1037 |
| 480 | 712973 | 392617 | 369411 | 312679 | 191303 | 116137 | 64888 | 34819 | 18795 | 12439 | 6384 | 1079 |
| 510 | 622275 | 339440 | 323655 | 282342 | 174756 | 106854 | 60168 | 32401 | 17426 | 11603 | 6048 | 1100 |
| 540 | 544737 | 294403 | 283647 | 255059 | 159870 | 98720 | 56112 | 30079 | 16271 | 10952 | 5714 | 1157 |
| 570 | 478681 | 257095 | 249556 | 231073 | 146335 | 91334 | 52145 | 28072 | 15183 | 10261 | 5406 | 1181 |

Figure 6:
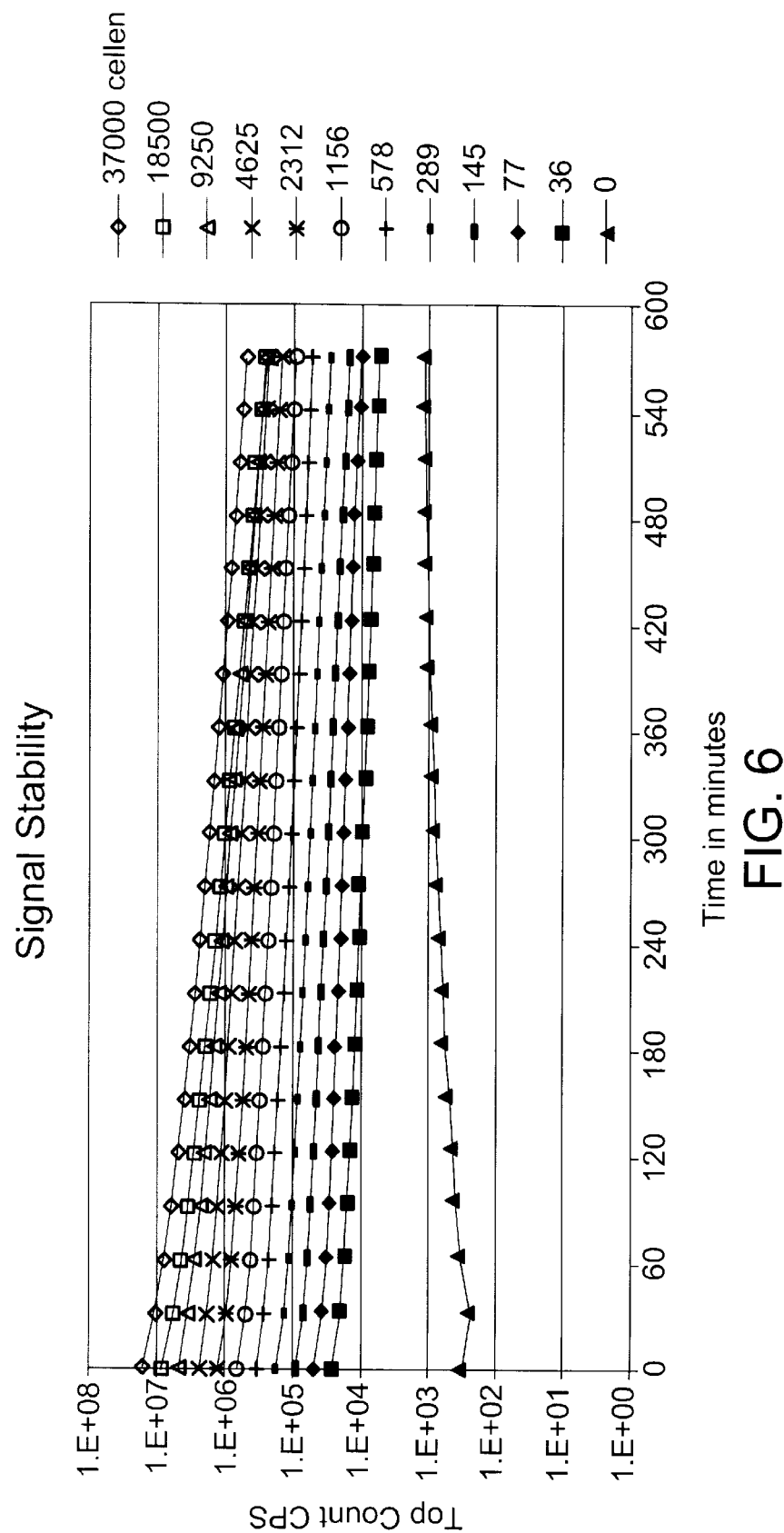
FIG. 6 is a graph demonstrating the relation between time measured in minutes (X-axis) and light intensity measured in counts per second (Y-axis).

The results demonstrate that the light signal correlates to the number of cells, but that the rate of decrease of the light signal depends on the number of cells. The half-life at high cell numbers is approximately 1 hour. This time increases according as fewer cells are present (see also FIG. 6).

By splitting up Solution C into two parts, Solution D and Solution E, and adding them successively to a cell suspension, a system can be made of which the rate of decrease of the light signal is independent of the number of cells.

| Formulation Solution D: | |
|---|---|
| Triton N-101 | 4 gram per liter |
| NaOH | 100 mM |

| Formulation Solution E: | |
|---|---|
| HEPES | 350 mM |
| EDTA | 4 mM |
| MgCl2 | 4 mM |
| NaCl | 130 mM |
| NaH2PO4 | 150 mM |
| BSA | 3.0 gram per liter |
| Trehalose | 10.0 gram per liter |
| D-Luciferin | 0.4 mM |
| Luciferase | 12 milligram per liter |
| pH set at 7.4 with NaOH | |

For this purpose, a dilution series (1:2) was made from CHO (Chinese Hamster Ovary) cells in Dulbecco's MEM supplemented with Fetal Calf Serum (FCS) to 10% end concentration from 37000 cells per 100 μl to 36 cells per 100 μl in a white "tissue culture treated" microplate. To 100 μl of each cell dilution, 50 μl of Solution D was added and the microplate was shaken for about 2 minutes. Next, 50 μl of Solution E was added hereto and shaken once again. The ATP-dependent light signal was repeatedly measured in time on a Packard TopCount for 9.5 hours.

The results are as follows:

| Time | Cell number per 100 μl DMEM, 10% FKS | | | | | | | | | | | |
|---|---|---|---|---|---|---|---|---|---|---|---|---|
| (min) | 37000 | 18500 | 9250 | 4625 | 2313 | 1156 | 578 | 289 | 145 | 72 | 36 | 0 |
| 0 | 15926607 | 9265862 | 5064576 | 2701038 | 1377222 | 729482 | 377677 | 201242 | 107055 | 54417 | 30508 | 476 |
| 30 | 15266667 | 8565421 | 4633551 | 2466607 | 1258022 | 666151 | 345293 | 183669 | 96291 | 49516 | 27265 | 362 |
| 60 | 14260000 | 7866295 | 4254332 | 2273127 | 1159500 | 613956 | 317827 | 169234 | 88363 | 45655 | 25126 | 319 |
| 90 | 13343333 | 7273971 | 3934740 | 2107094 | 1075668 | 569032 | 294829 | 157511 | 81935 | 42201 | 23379 | 292 |
| 120 | 12473333 | 6749126 | 3655833 | 1961272 | 1001506 | 528935 | 274806 | 147387 | 76893 | 39225 | 22192 | 273 |
| 150 | 11666667 | 6267367 | 3398278 | 1822955 | 932186 | 492629 | 256308 | 137758 | 71842 | 36445 | 20962 | 260 |
| 180 | 10900000 | 5824752 | 3160377 | 1697725 | 868001 | 458433 | 239121 | 129036 | 67342 | 33961 | 20084 | 243 |
| 210 | 10170000 | 5425512 | 2944913 | 1582163 | 808965 | 426978 | 223166 | 120719 | 63158 | 31531 | 19098 | 229 |
| 240 | 9499379 | 5053815 | 2742458 | 1475159 | 754209 | 398221 | 208299 | 112792 | 59781 | 29540 | 18104 | 229 |
| 270 | 8881891 | 4709434 | 2555135 | 1373624 | 703270 | 370603 | 194672 | 105689 | 56624 | 27415 | 17170 | 228 |
| 300 | 8286678 | 4391574 | 2379784 | 1281135 | 656101 | 345122 | 181686 | 98815 | 53510 | 25638 | 16183 | 218 |
| 330 | 7753348 | 4097355 | 2220083 | 1195051 | 612369 | 322145 | 170040 | 92561 | 50709 | 23823 | 15318 | 221 |
| 360 | 7249262 | 3824937 | 2070513 | 1114717 | 571713 | 300295 | 158893 | 86465 | 48232 | 22270 | 14375 | 214 |
| 390 | 6782170 | 3572479 | 1932779 | 1040446 | 534360 | 280340 | 148864 | 81022 | 45735 | 20814 | 13719 | 212 |
| 420 | 6353719 | 3342239 | 1805662 | 973250 | 499430 | 262197 | 139251 | 76002 | 43376 | 19535 | 12818 | 220 |
| 450 | 5946932 | 3125245 | 1687138 | 908086 | 467072 | 244972 | 130067 | 71109 | 40732 | 18211 | 12120 | 211 |
| 480 | 5579366 | 2923640 | 1576153 | 849185 | 436177 | 228964 | 121946 | 66829 | 38820 | 17005 | 11397 | 209 |

-continued

| Time (min) | \multicolumn{12}{c}{Top Count CPS (counts per second) Cell number per 100 μl DMEM, 10% FKS} |

| Time (min) | 37000 | 18500 | 9250 | 4625 | 2313 | 1156 | 578 | 289 | 145 | 72 | 36 | 0 |
|---|---|---|---|---|---|---|---|---|---|---|---|---|
| 510 | 5232171 | 2736005 | 1473761 | 793583 | 408269 | 214142 | 114224 | 62631 | 36733 | 15963 | 10582 | 213 |
| 540 | 4908614 | 2561487 | 1377321 | 742845 | 382487 | 200094 | 106784 | 58884 | 34706 | 14993 | 9992 | 210 |
| 570 | 4612006 | 2401882 | 1289080 | 695193 | 358281 | 187441 | 100059 | 55115 | 32806 | 14008 | 9323 | 212 |

Figure 7:
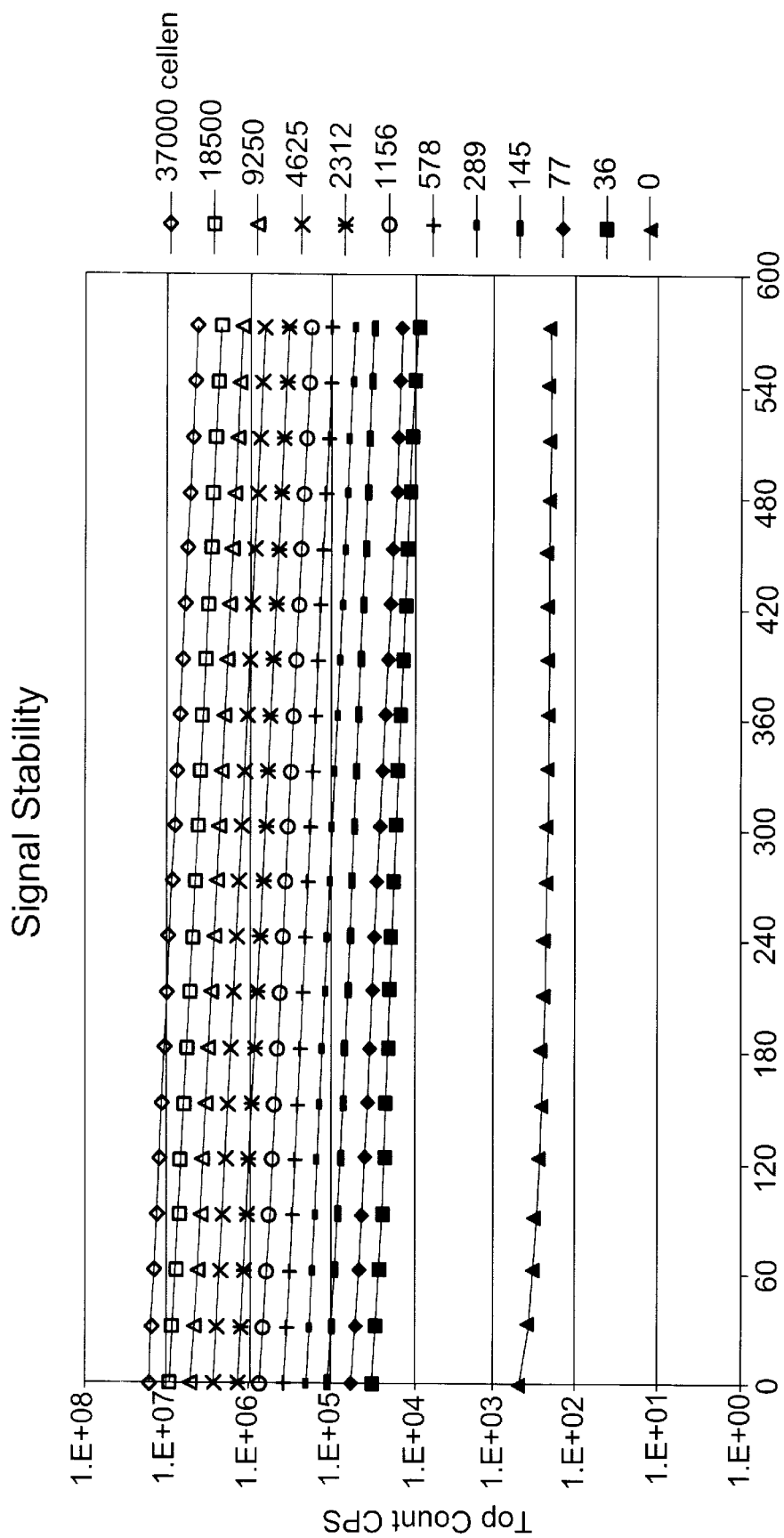
FIG. 7 is a graph demonstrating the relation between time measured in minutes (X-axis) and light intensity measured in counts per second (Y-axis).

From the results, it follows that the light signal correlates linearly to the number of cells. Now, too, the rate of decrease of the signal has become independent of the number of cells. In this example, the half-life is approximately 5 hours (see also FIG. 7).

What is claimed is:

1. A method for detecting ATP in a sample, wherein the sample is contacted with a reaction mixture to effect a light signal, the reaction mixture comprising luciferin, luciferase and one or more water-soluble salts, the total salt concentration being at least 0.05 mole/liter, and wherein the light signal is measured to indicate the presence or absence of the ATP in said sample.

2. A method according to claim 1, wherein the total salt concentration is at least 0.10 mole/liter.

3. A method according to claim 1, wherein the salts are selected from alkali salts or earth alkaline salts of $Cl^-$, $Br^-$, $SO_4^{2-}$, $HSO_4^-$, $HPO_4^{2-}$, $H_2PO_4^-$, $NO_3^-$ and $HCO_3^-$.

4. A method according to claim 1, wherein the reaction mixture also contains a buffer maintaining the reaction mixture at a pH of between 6.5 and 8.2.

5. A method according to claim 1, wherein the sample contains cells, and the cells being priorly subjected to cell lysis in an alkaline medium.

6. A method according to a claim 5, wherein the cell lysis takes place utilizing a lysing detergent.

7. A method according to claim 6, wherein the lysing detergent is a nonionic detergent.

8. A method according to claim 7, wherein the cell lysis is carried out at a pH greater than 9.5.

9. A kit for use in a method according to claim 1, comprising a mixture of luciferin and luciferase and a buffer solution comprising salts.

10. A kit according to claim 9, wherein the mixture of luciferase and luciferase is present is lyophilized form.

11. A kit according to claim 10, also comprising a cell lysis solution, said solution comprising a lysing detergent and having a pH of above 9.5.

12. A method according to claim 2, wherein the salts are selected from alkali salts or earth alkaline salts of $Cl^-$, $Br^-$, $SO_4^{2-}$, $HSO_4^-$, $HPO_4^{2-}$, $H_2PO_4^-$, $NO_3^-$ and $HCO_3^-$.

13. A method according to claim 12, wherein the reaction mixture also contains a buffer maintaining the reaction mixture at a pH of between 6.5 and 8.2.

14. A method according to claim 13, wherein the sample contains cells, and the cells being priorly subjected to cell lysis in an alkaline medium.

15. A method according to claim 14, wherein the cell lysis takes place utilizing a lysing detergent.

16. A method according to claim 15, wherein the lysing detergent is a nonionic detergent.

17. A method according to claim 16, wherein the cell lysis is carried out at a pH greater than 9.5.

18. A composition for detecting ATP in a sample comprising a total salt concentration of at least 0.05 mole/liter for prolonging a light signal occurring in a luciferin-luciferase reaction.

* * * * *